(12) United States Patent
Bouzari

(10) Patent No.: US 11,830,276 B2
(45) Date of Patent: Nov. 28, 2023

(54) ULTRASONIC BIOMETRIC IMAGING SYSTEM AND METHOD FOR CONTROLLING THE ULTRASONIC BIOMETRIC IMAGING SYSTEM

(71) Applicant: Fingerprint Cards Anacatum IP AB, Gothenburg (SE)

(72) Inventor: Hamed Bouzari, København Ø (DK)

(73) Assignee: FINGERPRINT CARDS ANACATUM IP AB, Gothenburg (SE)

(*) Notice: Subject to any disclaimer, the term of this patent is extended or adjusted under 35 U.S.C. 154(b) by 0 days.

(21) Appl. No.: 17/760,630

(22) PCT Filed: Sep. 8, 2020

(86) PCT No.: PCT/SE2020/050845
§ 371 (c)(1),
(2) Date: Mar. 15, 2022

(87) PCT Pub. No.: WO2021/061036
PCT Pub. Date: Apr. 1, 2021

(65) Prior Publication Data
US 2022/0335744 A1    Oct. 20, 2022

(30) Foreign Application Priority Data

Sep. 24, 2019 (SE) .................... 1951073-4

(51) Int. Cl.
*G06V 40/13* (2022.01)
*G06F 3/043* (2006.01)
(52) U.S. Cl.
CPC .......... *G06V 40/1306* (2022.01); *G06F 3/043* (2013.01)
(58) Field of Classification Search
CPC .... G06V 40/1306; G06F 3/043; A61B 5/1172
See application file for complete search history.

(56) References Cited

U.S. PATENT DOCUMENTS 6,126,602 A * 10/2000 Savord ................ G01S 15/8925
600/443
9,984,271 B1    5/2018 King et al.
(Continued)

FOREIGN PATENT DOCUMENTS

EP    1046928 A2    10/2000
EP    3086261 A2    10/2016
(Continued)

OTHER PUBLICATIONS

Extended European Search Report dated Sep. 13, 2022 for European Application No. 20868512.3, 8 pages.
(Continued)

*Primary Examiner* — Jonathan A Boyd
(74) *Attorney, Agent, or Firm* — Westman, Champlin & Koehler, P.A.

(57) ABSTRACT

The invention relates to an ultrasonic biometric imaging system comprising: a cover structure having a touch surface; a plurality of ultrasonic transducers arranged at a periphery of the touch surface; a plurality of mixed-signal integrated circuits configured to: AD-convert a received analog echo-signal to form a digital echo signal for each active ultrasonic transducer in the subset of ultrasonic transducers; perform local beamforming by introducing a first controllable delay to each digital echo signal to form a plurality of delayed echo signals; and sum the delayed echo signals to form an intermediate signal. The biometric imaging system further comprises a host processor connected to each of the plurality of mixed-signal integrated-circuits and configured to: receive intermediate signals from the of mixed-signal integrated-circuits; perform global beamforming by introducing a second controllable delay to each intermediate signal; and sum the delayed intermediate signals to form a final echo signal.

16 Claims, 7 Drawing Sheets

(56) References Cited

U.S. PATENT DOCUMENTS

| | | |
|---|---|---|
| 10,198,610 B1 * | 2/2019 | Yousefpor .............. B06B 1/0622 |
| 2015/0189136 A1 | 7/2015 | Chung et al. |
| 2017/0053151 A1 | 2/2017 | Yazandoost et al. |
| 2017/0090028 A1 | 3/2017 | Djordjev et al. |
| 2017/0326593 A1 | 11/2017 | Garlepp et al. |
| 2019/0005300 A1 | 1/2019 | Garlepp et al. |

FOREIGN PATENT DOCUMENTS

| | | |
|---|---|---|
| WO | 2015009635 A1 | 1/2015 |
| WO | 2016160981 A1 | 10/2016 |
| WO | 2017052836 A1 | 3/2017 |
| WO | 2019125273 A1 | 6/2019 |
| WO | 2019203383 A1 | 10/2019 |

OTHER PUBLICATIONS

Van Veen, B. et al., "Beamforming Techniques for Spatial Filtering," 2000 CRC Press LLC, , retrieved on Aug. 31, 2022, 23 pages.

Van Veen, B.D. et al., "Beamforming: A Versatile Approach to Spatial Filtering," IEEE ASSP Magazine, vol. 5, No. 2, Apr. 1988, pp. 4-24.

International Search Report and Written Opinion for International Application No. PCT/SE2020/050845 dated Oct. 22, 2020 (11 pages).

\* cited by examiner

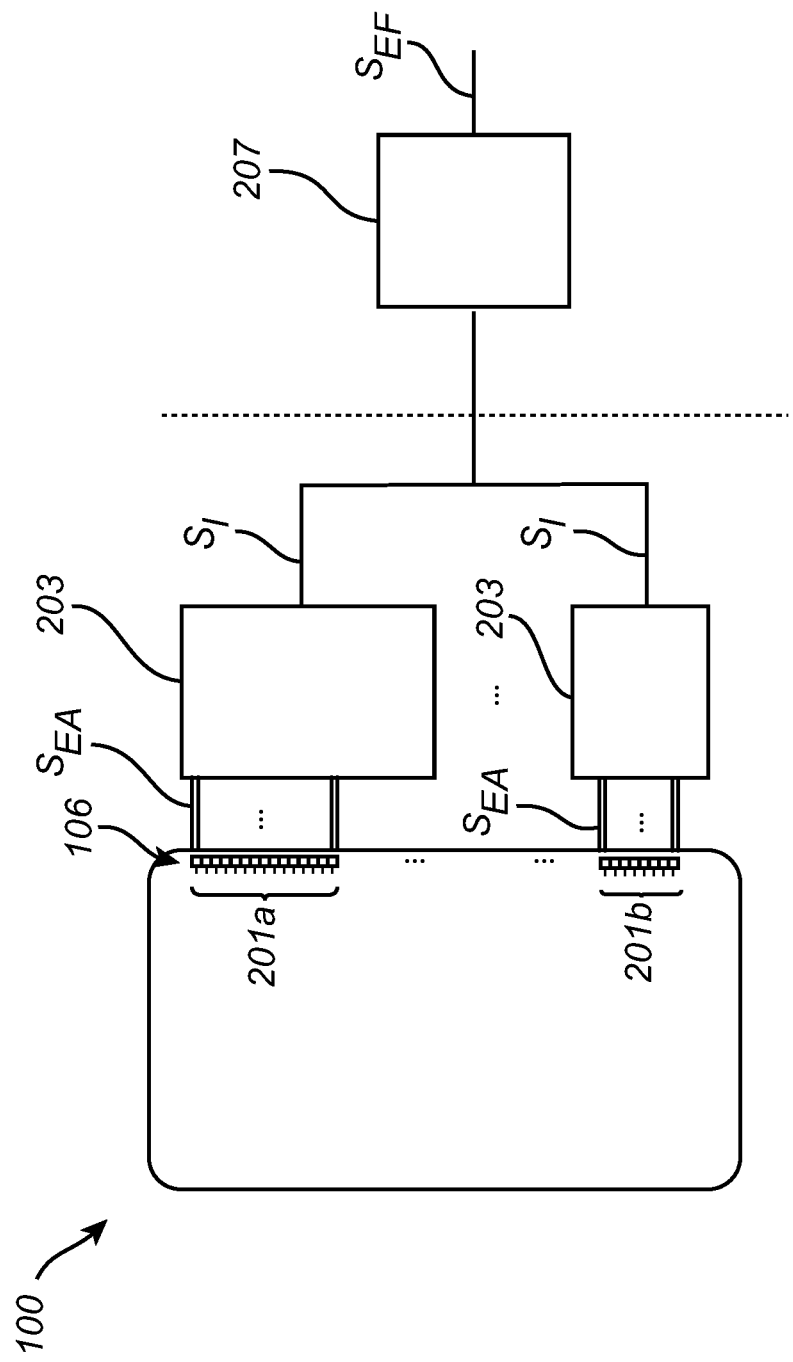

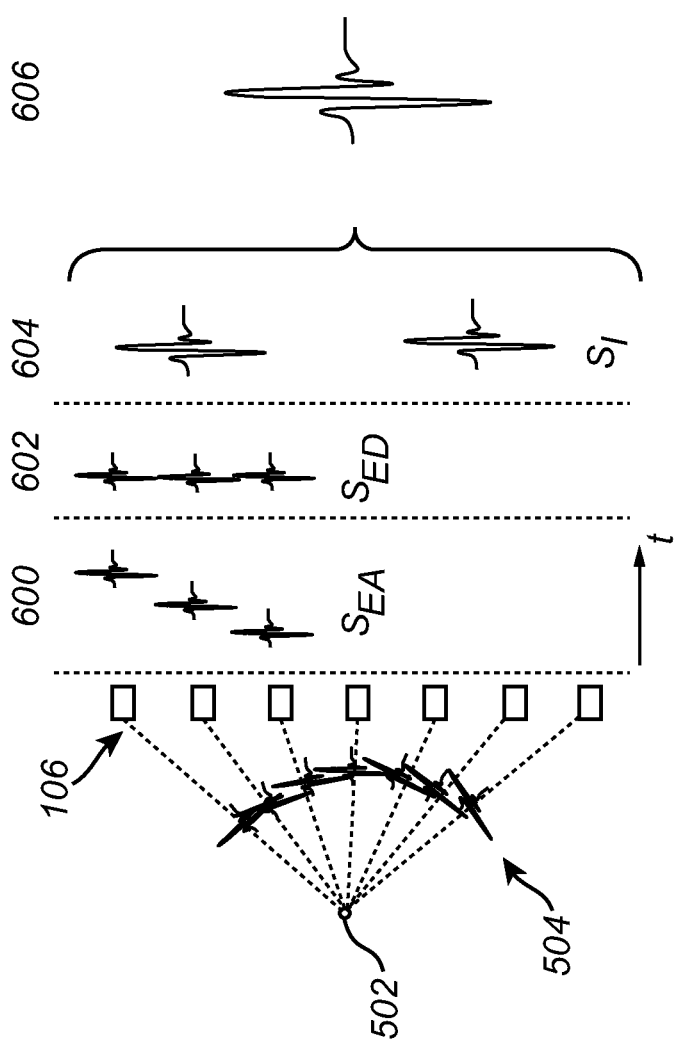

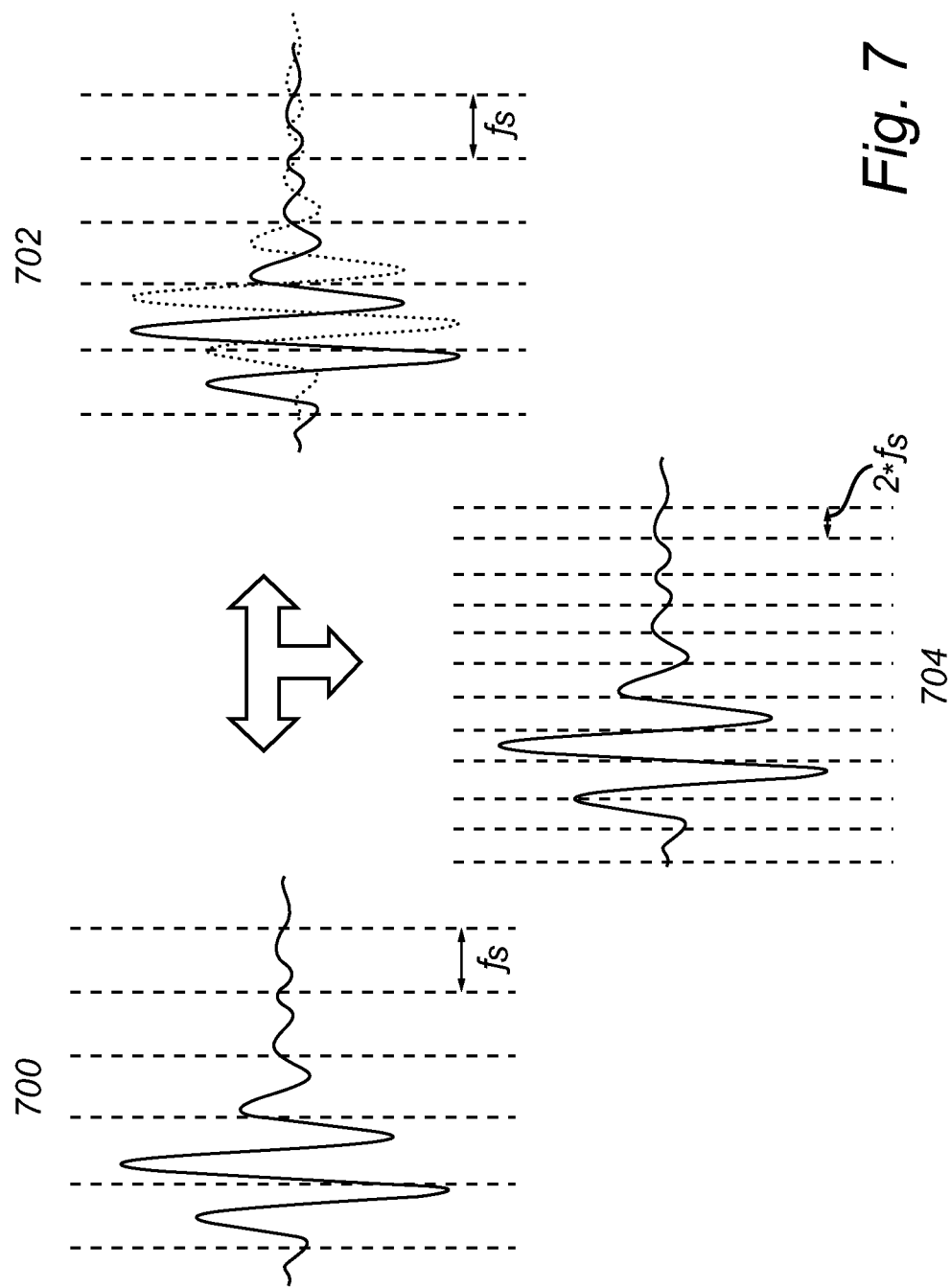

ULTRASONIC BIOMETRIC IMAGING
SYSTEM AND METHOD FOR
CONTROLLING THE ULTRASONIC
BIOMETRIC IMAGING SYSTEM

CROSS-REFERENCE TO RELATED
APPLICATIONS

This application is a 371 U.S. National Stage of International Application No. PCT/SE2020/050845, filed Sep. 8, 2020, which claims priority to Swedish Patent Application No. 1951073-4, filed Sep. 24, 2019. The disclosures of each of the above applications are incorporated herein by reference in their entirety.

FIELD OF THE INVENTION

The present invention relates to an ultrasonic biometric imaging system and to a method for image acquisition in such a system. In particular, the present invention relates to beamforming in an ultrasonic imaging system suitable for fingerprint imaging.

BACKGROUND OF THE INVENTION

Biometric systems are widely used as means for increasing the convenience and security of personal electronic devices, such as mobile phones etc. Fingerprint sensing systems in particular are now included in a large proportion of all newly released personal communication devices, such as mobile phones.

Due to their excellent performance and relatively low cost, capacitive fingerprint sensors have been used in an overwhelming majority of all biometric systems.

Among other fingerprint sensing technologies, ultrasonic sensing also has the potential to provide advantageous performance, such as the ability to acquire fingerprint (or palmprint) images from very moist fingers etc.

One class of ultrasonic fingerprint systems of particular interest are systems in which acoustic signals are transmitted along a surface of a device element to be touched by a user, and a fingerprint (palmprint) representation is determined based on received acoustic signals resulting from the interaction between the transmitted acoustic signals and an interface between the device member and the user's skin.

Such ultrasonic fingerprint sensing systems, which are, for example, generally described in US 2017/0053151 may provide for controllable resolution, and allow for a larger sensing area, which may be optically transparent, without the cost of the fingerprint sensing system necessarily scaling with the sensing area and thereby allowing integration of ultrasonic fingerprint sensors in a display of a device.

However, current solutions struggle to provide a high-resolution fingerprint with a large coverage area of the full in-display screen, as it is difficult to handle and process the large amount of RF-data generated for each touch event and thereby apply the image reconstruction and matching procedures required.

Accordingly, there is a need for improved methods and systems for large area fingerprint imaging using ultrasonic technology.

SUMMARY

In view of above-mentioned and other drawbacks of the prior art, it is an object of the present invention to provide an ultrasonic biometric imaging system and a method for imaging in ultrasonic biometric imaging system which provides improved imaging while reducing the computational load the imaging process.

According to a first aspect of the invention, there is provided an ultrasonic biometric imaging system comprising: a cover structure having a touch surface; a plurality of ultrasonic transducers arranged at a periphery of the touch surface, the plurality of ultrasonic transducers being configured to emit an ultrasonic beam in the cover structure and to receive reflected ultrasonic echo signals, the reflected ultrasonic echo signals resulting from reflections by an object in contact with the touch surface; a plurality of mixed-signal integrated-circuits, each mixed-signal integrated-circuit being connected to a subset of ultrasonic transducers.

Each mixed-signal integrated-circuit is configured to: analog-to-digital (AD)-convert a received analog echo-signal to form a digital echo signal for each active ultrasonic transducer in the subset of ultrasonic transducers; perform local beamforming by introducing a first controllable delay to each digital echo signal to form a plurality of delayed echo signals; and sum the plurality of delayed echo signals to form an intermediate signal.

The biometric imaging system further comprises: a host processor connected to each of the plurality of mixed-signal integrated-circuits and configured to: receive a plurality of intermediate signals from the plurality of mixed-signal integrated-circuits; perform global beamforming by introducing a second controllable delay to each intermediate signal; and sum the plurality of delayed intermediate signals to form a final echo signal.

The ultrasonic transducers typically comprise a piezoelectric material generating an ultrasonic signal in response to an electric field applied across the material by means of the top and bottom electrodes. In principle, it is also possible to use other types of ultrasonic transducers, such as capacitive micromachined ultrasonic transducers (CMUT). The ultrasonic transducers will be described herein as transceivers being capable of both transmitting and receiving ultrasonic signals. However, it is also possible to form a system comprising individual and separate ultrasonic transmitters and receivers.

The device is further considered to comprise ultrasonic transducer control circuitry configured to control the transmission and reception of ultrasonic signals and considered to comprise appropriate signal processing circuitry required for extracting an image from the received ultrasonic echo signals.

In order to reconstruct an image from the RF data that results from the echo signals received by the transducers, the data need to be transferred to the host, which demands a large amount of memory as well as a high bandwidth channel for transmitting the data.

The ultrasonic signals can be described by radio frequency data, RF-data. The radio spectrum may encompass frequencies from 3 Hz up to 3 THz, and for ultrasonic signals the applicable frequency range is approximately 20 kHz up to several GHz, such as 3 GHz. Accordingly, the received RF-data describes an oscillating signal resulting from the echo of the emitted ultrasonic beam. Which ultrasonic frequency or frequency range to use is determined based on the application at hand and may vary depending on parameters such as required resolution, type of transducer, material in which the ultrasonic signal will propagate, power consumption requirements etc.

In view of the above, the present invention is based on the realization that the task of receive-side beamforming can be divided into a number of smaller but parallel beamforming tasks. Thereby, it is possible to lower the amount of data that has to be transferred from the mixed-signal integrated circuit to the host processor or elsewhere within the system. An additional advantage is that the computational load is distributed between the mixed-signal integrated circuits and the host processor.

The mixed signal integrated circuit, which may be an ASIC, is part of the front-end circuitry physically located close to the transducers. The host processor on the other hand is located at a greater distance from the transducers. The host processor may for example be a processing unit of a smartphone or tablet computer in which the biometric imaging system is arranged.

For any position in the imaging area, a delay profile has to be applied to the received and recorded echo signals in order to beamform or reconstruct the pixel value corresponding to that position. If the beamforming was to be performed in the host processor, large amounts of data would have to be transmitted to the host processor, requiring high bandwidth data channels. Moreover, the host processor can also be expected to at least periodically be occupied with other tasks, which will delay the processing of data from the transducers and in turn make the biometric imaging slower. Instead, according to the resent invention, this beamforming task can be split into two parts which can be done faster, and which demands less processing power as well as reducing the requirement of high-bandwidth data channels between the mixed-signal integrated circuit and the host processor.

According to one embodiment of the invention, the first controllable delay is an individually controllable delay applied to each digital echo signal to form the plurality of delayed echo signals. Each echo signal represents an echo of a transmitted signal from a transducer, and since the travel time for the echo signal is different depending on the location transducer used, each delay has to be controlled individually in order to form a signal representing a selected pixel, i.e. a selected position of the sensing surface. The first delay introduced by the mixed-signal integrated circuit can be seen as a "micro-delay" or local delay which is applied to a subset of received echo-signals, thereby forming the intermediate signal representing a subset of the received signal.

According to one embodiment of the invention, the second controllable delay is an individually controllable delay applied to each intermediate signal to form the plurality of delayed intermediate signals. The delay applied to the intermediate signal can be seen as a "macro-delay" or a global delay, and it is larger than the "micro-delay" introduced in the first stage by the mixed-signal circuit. Thereby a distributed two-stage receive-side beamforming is achieved.

According to one embodiment of the invention, the first and second controllable delays introduced during local and global beamforming, respectively, are configured such that the resulting final echo signal represents one pixel of the ultrasonic biometric imaging system. Thereby, the beamforming process can be said of define the pixel of the image. Accordingly, each pixel over and along a central axis line of the transmitted ultrasonic beam can be beamformed after each other, with closer pixel points being beamformed earlier than the pixel points located farther away. The beamforming is carried out while the acoustic echo signals are arriving back to the transducer elements. In other words, instead of sending the received echo signals from each element back to the host processor to be processed for beamforming, several intermediate signals can be sent to the host.

According to one embodiment of the invention, the mixed-signal integrated circuit is further configured to interpolate the digital echo signal. Since the sampling frequency of the mixed-signal integrated circuit is limited, interpolation can be used to improve the quality of the sampled signal. The interpolation may be required to calculate the value of the signal at time instances which are in sub-samples, since using the nearest sample value instead of interpolation can lower the quality of the final beamformed image. Any one of a number of well-known interpolation methods can be used, such as spline or polynomial interpolation.

According to one embodiment of the invention, the plurality of mixed-signal integrated-circuits are advantageously configured to operate in parallel. Thereby, a plurality of intermediate signals can be formed simultaneously, reducing the time it takes to form the full image. It is also possible to employ parallelism for the global beamforming performed in the host processor, for example if the processor is a multi-core processor and/or if the processor is capable of running several threads in parallel.

According to one embodiment of the invention, the ultrasonic transducers are configured to introduce a controllable emission delay between consecutive emitted ultrasonic beams, wherein the controllable emission delay is shorter than a period of a sampling frequency of the mixed-signal circuit. The effective sampling frequency of the system can be increased by transmitting two or more emissions with a controllable delay between consecutive emitted beams. Thereby, by using the same actual sampling frequency in the mixed-signal integrated circuit, each sampled signal of the time shifted signals will acquire a different part of the received signal. Finally, by combining the sampled time shifted echo signals, the received signal has synthetically been sampled at a higher sampling frequency. The described method can be referred to as "equivalent time sampling" and it can advantageously be used to increase the effective sampling frequency of the mixed-signal integrated circuit without changing the hardware or the operating frequency of the circuitry.

There is also provided an electronic user device comprising an ultrasonic biometric imaging system according to any one of the preceding claims, where the cover structure of the ultrasonic biometric imaging system may be a display glass of the electronic user device. The display may be any one of a number of known display types, such an OLED, LED, LCD, AMOLED or the like as long as the display comprises a cover structure such as a cover glass which is capable of ultrasonic wave propagation.

According to a second aspect of the invention, there is provided a method for image acquisition in an ultrasonic biometric imaging device comprising a cover structure having a touch surface and a plurality of ultrasonic transducers arranged at a periphery of the touch surface. The method comprises: emitting, by the plurality of ultrasonic transducers, an ultrasonic beam in the cover structure; receiving, by the plurality of ultrasonic transducers, reflected ultrasonic echo signals, the reflected ultrasonic echo signals resulting from reflections by an object in contact with the touch surface; AD-converting, in a mixed-signal integrated circuit connected to a subset of ultrasonic transducers, a received analog echo-signal and forming a digital echo signal for each active ultrasonic transducer in the subset of ultrasonic transducers; performing local beamforming by introducing a first controllable delay to each digital echo signal, thereby forming a plurality of delayed echo signals; and summing the plurality of delayed echo signals forming an intermediate signal; receiving, by a host processor connected to each of the plurality of mixed-signal integrated-circuits, a plurality of intermediate signals from the plurality of mixed-signal integrated-circuits; performing, by the host processor, global beamforming by introducing a second controllable delay to each intermediate signal; and summing, by the host processor, the plurality of delayed intermediate signals, thereby forming a final echo signal.

Effects and features of the second aspect of the invention are largely analogous to those described above in connection with the first aspect of the invention.

Further features of, and advantages with, the present invention will become apparent when studying the appended claims and the following description. The skilled person realize that different features of the present invention may be combined to create embodiments other than those described in the following, without departing from the scope of the present invention.

BRIEF DESCRIPTION OF THE DRAWINGS

These and other aspects of the present invention will now be described in more detail, with reference to the appended drawings showing an example embodiment of the invention, wherein:

FIG. 2 schematically illustrates a biometric imaging device according to an embodiment of the invention FIG. 3 schematically illustrates a biometric imaging device according to an embodiment of the invention;

FIG. 6 schematically illustrates features of a biometric imaging device according to an embodiment of the invention; and FIG. 7 schematically illustrates a feature of a biometric imaging device according to an embodiment of the invention.

DETAILED DESCRIPTION OF EXAMPLE EMBODIMENTS

In the present detailed description, various embodiments of the system and method according to the present invention are mainly described with reference to an ultrasonic biometric imaging device configured to acquire an image of a biometric feature such as a fingerprint or palmprint when a finger or a palm is placed in contact with the touch surface. The touch surface may for example be a surface of a display cover glass in a smartphone, tablet or the like. However, the described method can equally well be implemented in other devices, such as an interactive TV, meeting-table, smartboard, information terminal or any other device having a cover structure where ultrasonic waves can propagate. Since the transducers are arranged at the periphery of the active touch surface, the described method can also be employed in e.g. an interactive shop window or a display cabinet in a store, museum or the like. The biometric object may in some applications be the cheek or ear of a user.

Figure 1A:
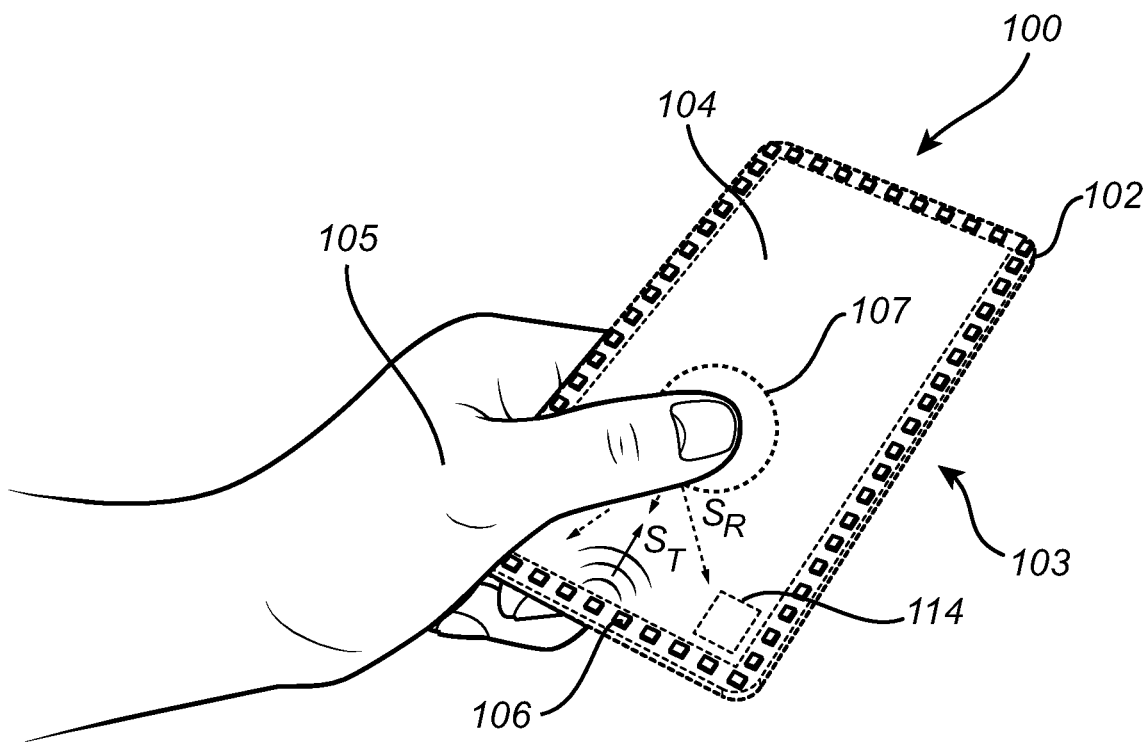
FIGS. 1A-B schematically illustrate a biometric imaging device according to an embodiment of the invention.

FIG. 1A schematically illustrates an ultrasonic biometric imaging system 100 integrated in an electronic device in the form of a smartphone 103. The illustrated smartphone 100 comprises a display panel having a cover structure 102 in the form of a cover glass 102. The cover glass 102 defines an exterior surface 104 configured to be touched by a finger 105, herein referred to as the touch surface 104. The cover structure 102 is here illustrated as a transparent cover glass of a type commonly used in a display panel of the smartphone 103. However, the cover structure 102 may equally well be a non-transparent cover plate as long as the acoustic properties of the cover structure 102 allows for propagation of ultrasound energy.

The display arrangement further comprises a plurality of ultrasonic transducers 106 connected to the cover structure 102 and located at the periphery of the cover structure 102. Accordingly, the ultrasonic transducers 106 are here illustrated as being non-overlapping with an active sensing area 104 of the biometric imaging device formed by the ultrasonic transducers 106 and the cover structure 102. However, the ultrasonic transducers 106 may also be arranged and configured such that they overlap an active sensing area. FIG. 1A illustrates an example distribution of the transducers 106 where the transducers 106 are evenly distributed around the periphery of the cover structure 102 along all sides of the display panel. However, other transducer distributions are equally possible, such as arranging the transducers 106 on one, two or three sides of the display panel, and also irregular distributions are possible.

Figure 1B:
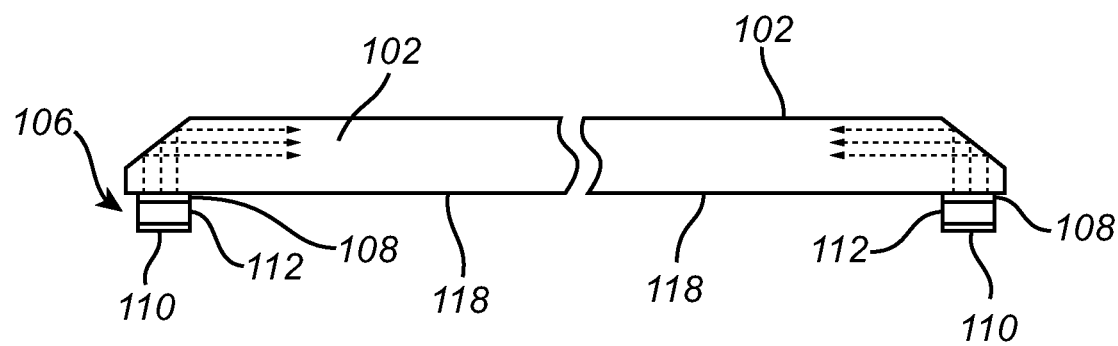

FIG. 1B is a cross section view of the cover structure 102 where it is illustrated that the ultrasonic transducers 106 are arranged underneath the cover structure 102 and attached to the bottom surface 118 of the cover structure 102. The ultrasonic transducer 106 is a piezoelectric transducer comprising a first electrode 108 and second electrode 110 arranged on opposing sides of a piezoelectric element 112 such that by controlling the voltage of the two electrodes 108, 110, an ultrasonic signal can be generated which propagates into the cover structure 102.

The pitch of the transducers may be between half the wavelength of the emitted signal and 1.5 times the wavelength, where the wavelength of the transducer is related to the size of the transducer. For an application where it is known that beam-steering will be required, the pitch may preferably be half the wavelength so that grating lobes are located outside of an active imaging area. A pitch approximately equal to the wavelength of the emitted signal may be well suited for applications where no beam-steering is required since the grating lobes will be close to the main lobe. The wavelength of the transducer should be approximately equal to the size of the features that are to be detected, which in the case of fingerprint imaging means using a wavelength in the range of 50-300 μm. An ultrasonic transducer 106 can have different configurations depending on the type of transducer and also depending on the specific transducer package used. Accordingly, the size and shape of the transducer as well as electrode configurations may vary. It is furthermore possible to use other types of devices for the generation of ultrasonic signals such as micromachined ultrasonic transducers (MUTs), including both capacitive (cMUTs) and piezoelectric types (pMUTs).

Moreover, suitable control circuitry 114 is required for controlling the transducer to emit an acoustic signal having the required properties with respect to e.g. amplitude, pulse shape and timing. However, such control circuitry for ultrasonic transducers is well known to the skilled person and will not be discussed in detail herein.

Each ultrasonic transducer 106 is configured to transmit an acoustic signal $S_T$ propagating in the cover structure 102 and to receive a reflected ultrasonic signal $S_R$ having been influenced by an object 105, here represented by a finger 105, in contact with the sensing surface 104.

The acoustic interaction signals $S_R$ are presently believed to mainly be due to so-called contact scattering at the contact area between the cover structure 102 and the skin of the user (finger 105). The acoustic interaction at the point of contact between the finger 105 and the cover plate 103 may also give rise to refraction, diffraction, dispersion and dissipation of the acoustic transmit signal $S_T$. Accordingly, the interaction signals $S_R$ are advantageously analyzed based on the described interaction phenomena to determine properties of the finger 105 based on the received ultrasonic signal. For simplicity, the received ultrasonic interaction signals $S_R$ will henceforth be referred to as reflected ultrasonic echo signals $S_R$. In some embodiments, the ultrasonic imaging system is configured to form an image of only a selected target area 107 of the touch surface, which is a selected portion of the entire touch area.

Accordingly, the ultrasonic transducers 106 and associated control circuitry 114 are configured to determine properties of the object 105 based on the received ultrasonic echo signal $S_R$. The plurality of ultrasonic transducers 106 are connected to and controlled by ultrasonic transducer control circuitry 114. The control circuitry 114 for controlling the transducers 106 may be embodied in many different ways. The control circuitry 114 may for example be one central control unit 114 responsible for determining the properties of the acoustic signals $S_T$ to be transmitted, and for analyzing the subsequent received ultrasonic echo signal $S_R$. Moreover, each transducer 106 may additionally comprise control circuitry for performing specified actions based on a received command.

The control unit 114 may include a microprocessor, microcontroller, programmable digital signal processor or another programmable device. The control unit 114 may also, or instead, include an application specific integrated circuit, a programmable gate array or programmable array logic, a programmable logic device, or a digital signal processor. Where the control unit 114 includes a programmable device such as the microprocessor, microcontroller or programmable digital signal processor mentioned above, the processor may further include computer executable code that controls operation of the programmable device. The functionality of the control circuitry 114 may also be integrated in control circuitry used for controlling the display panel or other features of the smartphone 100.

FIG. 2 is a system schematic illustrating further components of an ultrasonic biometric imaging system 100 according to an embodiment of the invention. The illustrated system 100 comprises a plurality of mixed-signal integrated-circuits 203, where each mixed-signal integrated circuit is connected to a subset of ultrasonic transducers 201a-b. The ultrasonic biometric imaging system 100 further comprises a host processor 207 connected to each of the plurality of mixed-signal integrated-circuits 203.

Figure 3:
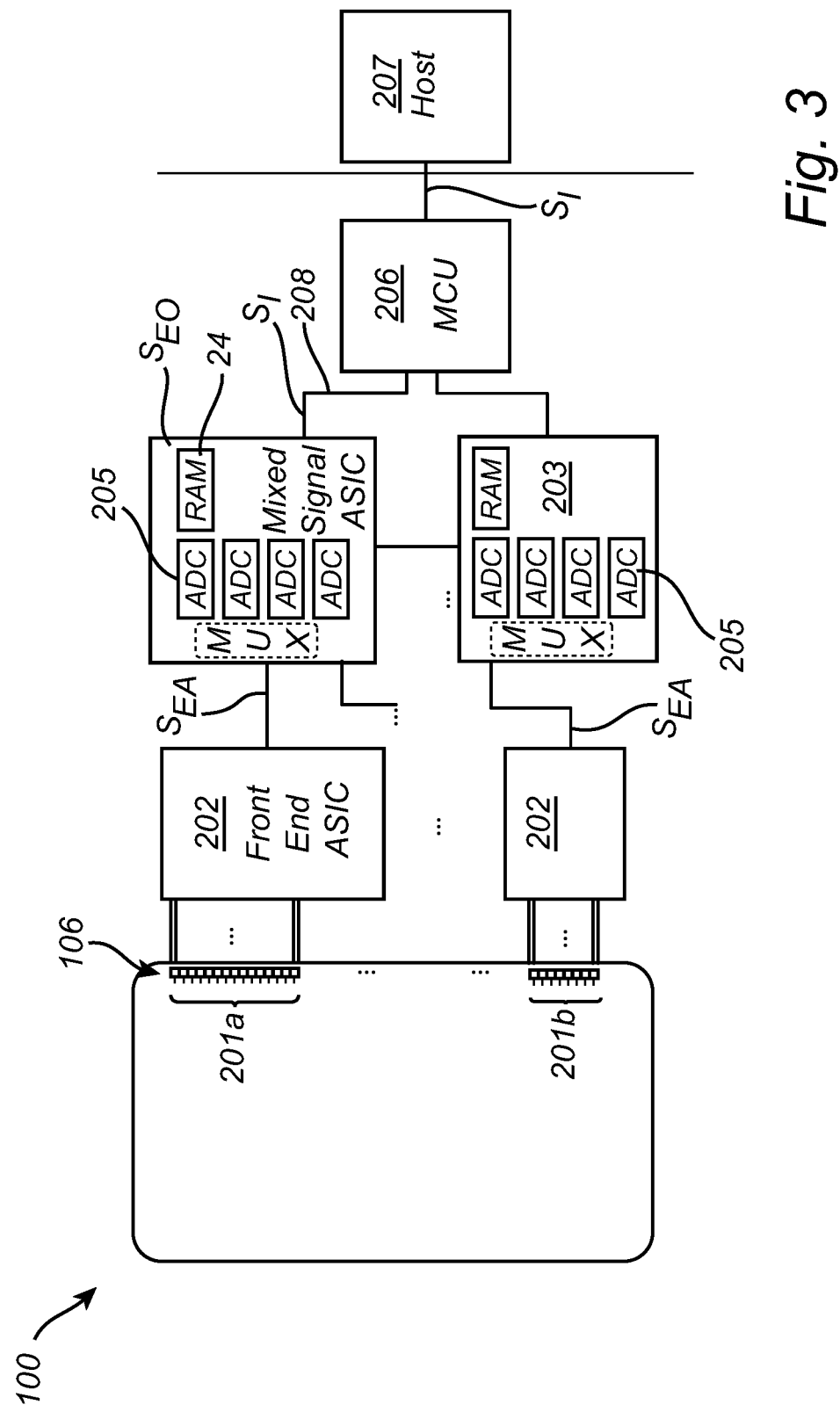

FIG. 3 illustrates an embodiment of the ultrasonic biometric imaging system 100, and its relation to the cover glass 102 and host processor 207 of the electronic device 103.

The system 100 comprises a plurality of transducers 106. The transducers 106 are grouped together into a plurality of subsets of transducers, herein represented by the subsets 201a and 201b, but the number of subsets 201 depends on the number of front-end ASICs 202 and mixed signal integrated circuits 203 in the system 100.

Each subset of transducers is here controlled by a respective front-end ASIC 202. The front-end ASIC 202 is also communicatively connected with a mixed-signal ASIC 203 and configured to forward analog signals SA from the transducers in the subset 201a-b to a corresponding mixed-signal ASIC 203. Each front-end ASIC 202 is typically communicatively connected with only one mixed-signal ASIC 203. For instance, up to eight, e.g. two to eight, front-end ASICs, each controlling its respective transducer subset 201a-b, may be connected to each mixed-signal ASIC 203 in the system 100.

The system 100 comprises a plurality of mixed-signal ASICs 203, each connected to a respective front-end ASIC 202 and configured to receive the respective analog signals SA representing the reflected ultrasonic echo signals from said plurality of front-end ASICs 202 and to convert the analogue echo signals SEA to digital echo signals $S_{ED}$ by means of at least one, preferably a plurality of, analog-to-digital converter(s) (ADC) 205 comprised in the mixed-signal ASIC, e.g. one ADC per front-end ASIC 202 connected to the mixed-signal ASIC 203 in cooperation with a multiplexer (MUX) for separating the respective analogue signals SEA from the different front-end ASICs. The plurality of digital echo signals $S_{ED}$ for a subset of transducers 201a are beamformed locally and summed to form an intermediate signal $S_I$ representing the subset of transducers 201a.

It would in principle be possible to combine the functionality of the front-end ASIC and the mixed-signal ASIC in one circuit. However, due to the higher voltage required for generating and transmitting ultrasonic signals, the AD-conversion circuitry would need to be properly shielded from the higher-voltage transmission circuitry.

Each mixed-signal ASIC 203 also comprises a data storage 204, in which the intermediate signal $S_I$ is stored in wait for being forwarded to the host 207. The mixed-signal ASICs may also be configured for controlling the overall timing of the respective transducer groups 201 connected thereto via front-end ASICs 202. In contrast to the front-end ASICs 202, which are typically not directly communicatively connected to each other, the mixed-signal ASICs may in some embodiments be connected with each other for direct communication there between.

The system 100 further comprises a microcontroller unit (MCU) 206, typically only one, with which all of the plurality of mixed-signal ASICs 203 in the sensor are communicatively connected. The MCU 206 may be configured for calculating the transducer configurations, e.g. defining and controlling during which time periods the transducers 106 should act as transmitters or receivers of ultrasonic waves. The MCU 206 may also be configured to control power management and timing of the transducers. The MCU 206 may be connected to the mixed-signal ASICs via at least one serial bus 208, preferably a plurality of serial buses, e.g. one serial bus 208 per mixed-signal ASIC 203. Further, the MCU 206 is connected to a host processor 207 via an interface 209, e.g. a Serial Peripheral Interface (SPI). The MCU 206 is configured to forward the digital intermediate signal $S_I$ from each of the mixed-signal ASICs 203, and previously stored in the respective data storages 24 thereof, to the host 207, where global beamforming is performed to form a final echo signal. Based on a plurality of final echo signals, one echo signal corresponding to one pixel, a fingerprint image can be obtained.

The host processor 207 may include a microprocessor, microcontroller, programmable digital signal processor or another programmable device. The host processor may also, or instead, include an application specific integrated circuit, a programmable gate array or programmable array logic, a programmable logic device, or a digital signal processor. Where the control unit includes a programmable device such as the microprocessor, microcontroller or programmable digital signal processor mentioned above, the processor may further include computer executable code that controls operation of the programmable device.

Figure 4:
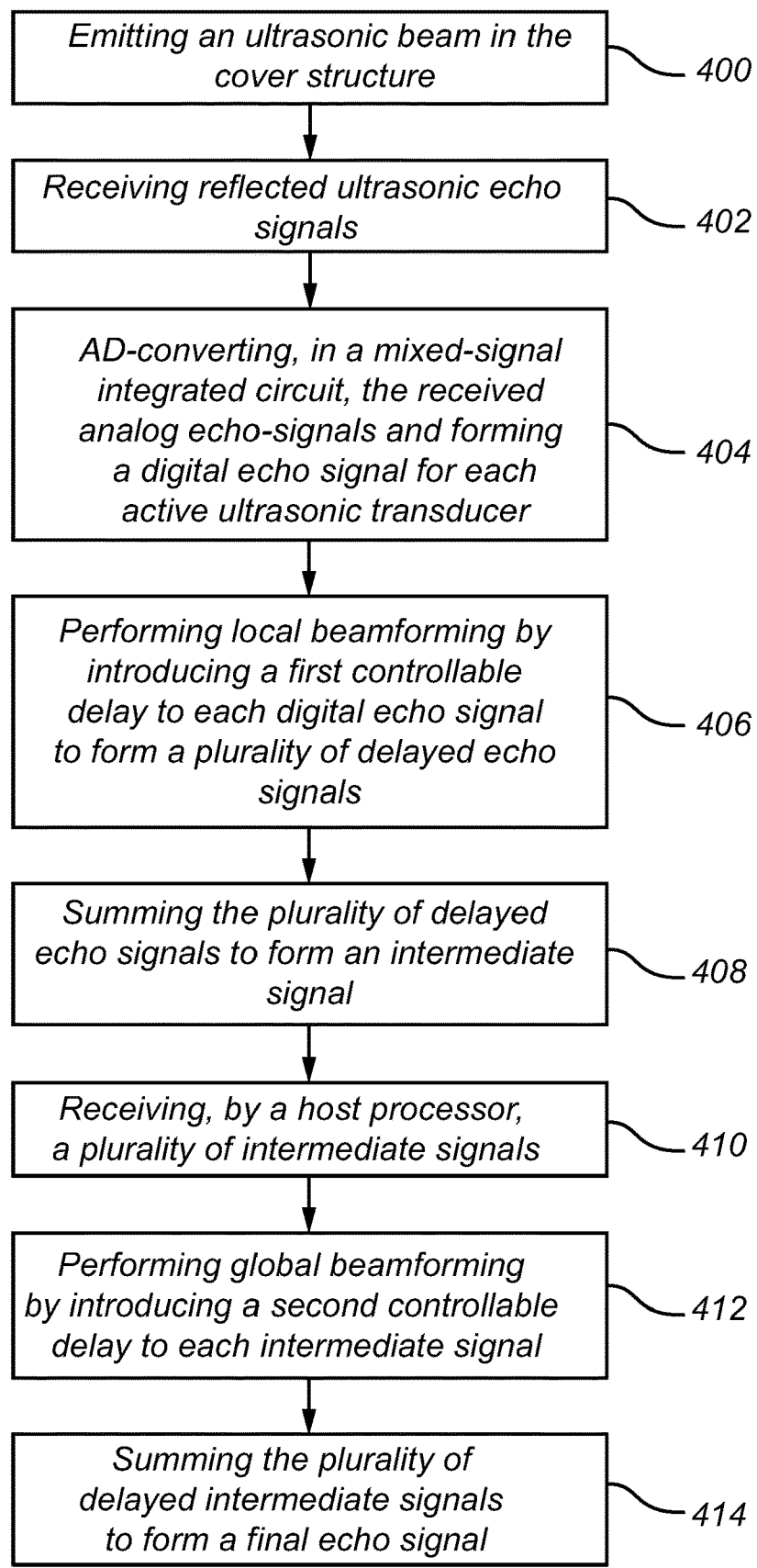
FIG. 4 is a flowchart outlining the general steps of a method according to an embodiment of the invention.
Figure 5:
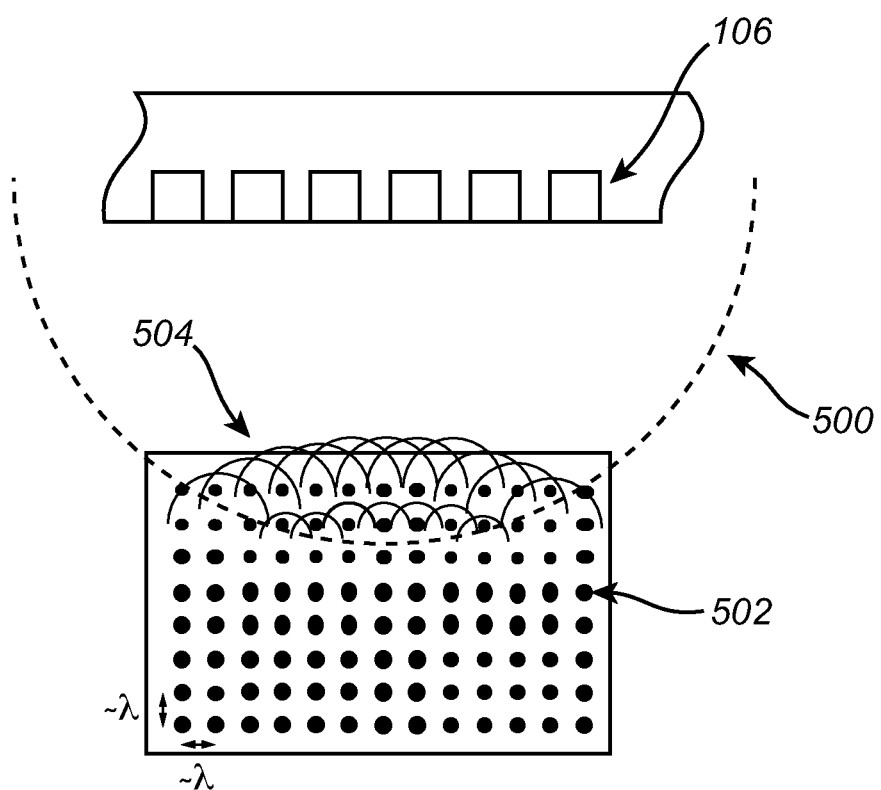
FIG. 5 schematically illustrates features of a biometric imaging device according to an embodiment of the invention.

FIG. 4 is a flow chart outlining the general steps of a method for image acquisition in an ultrasonic biometric imaging device according to an embodiment of the invention. The method will be described with reference to the biometric imaging systems illustrated in FIGS. 2 and 3 and with further reference to FIGS. 5-6 illustrating features of the biometric imaging system.

The method comprises emitting 400, by the plurality of ultrasonic transducers 106, an ultrasonic beam 500 in the cover structure 102. FIG. 5 schematically illustrates the emitted ultrasonic beam 500 as a wave propagating from a point source.

The next step comprises receiving 402, by the plurality of ultrasonic transducers 106, reflected ultrasonic echo signals 504, the reflected ultrasonic echo signals 504 resulting from reflections by an object in contact with the touch surface. Each point 502 in FIG. 5 is seen as an object reflecting a portion of the ultrasonic wave. A reflecting object may in reality be the ridge of a fingerprint which is in contact with the touch surface. The reflected ultrasonic echo signals 504 from one point 502 will reach the transducers at different times due to the difference in propagation distance. This is further illustrated by FIG. 6 where it is shown how reflected echo signals 504 from one point 502 of the touch surface propagates towards the plurality of transducers 106 and that they will reach the transducers at different points in time depending on the distance between the point 502 and the respective transducer. The point 502 may also be referred to as a pixel, since it is the receive side beamforming that will define which points are to be used when forming a resulting biometric image, and thereby also the resolution of the image. The transducer will convert the reflected ultrasonic echo signals into received analog echo signals SEA as illustrated in the first region 600 of FIG. 6.

The received analog echo-signals SEA are AD-converted 404 by a mixed-signal integrated circuit 203 connected to a subset of the plurality of ultrasonic transducers, and a digital echo signal is formed for each active ultrasonic transducer in the subset of ultrasonic transducers. The AD-conversion may also include interpolation of the AD-converted signals to improve the quality of the digital echo signal.

Next, local beamforming is performed 406 by introducing a first controllable delay to each digital echo signal, thereby forming a plurality of delayed echo signals $S_{ED}$ as illustrated in portion 602 of FIG. 6. The beamforming performed by the mixed-signal integrated circuit 203 is referred to as local beamforming since it the mixed-signal integrated circuits 203 are physically located close to the transducers, and also since the beamforming is performed for the subset of transducers and not for all of the transducers used to form the final biometric image. Each of the digital echo signals $S_{ED}$ is delayed by an amount so that the signals are aligned in time.

In the following step, the plurality of delayed echo signals are summed 408, forming an intermediate signal $S_I$ as illustrated in portion 604 of FIG. 6. As a result of the summation, the intermediate signal $S_I$ has a larger amplitude than the corresponding analog echo signals SEA.

The next steps comprise receiving 410, by the host processor 207 connected to each of the plurality of mixed-signal integrated-circuits, a plurality of intermediate signals $S_I$ from the plurality of mixed-signal integrated-circuits 203 and performing 412, global beamforming by introducing a second controllable delay to each intermediate signal $S_I$. The second controllable delay is typically larger than the first controllable delay since the effective time difference between the intermediate signals is larger than for the received analog echo-signals. The beamforming performed by the host processor is referred to as global beamforming both since the host processor is located at a greater distance from the transducers and since the global beamforming is the final beamforming step required for a given point of the touch surface.

The final step comprises summing 414 the plurality of delayed intermediate signals $S_I$, thereby forming a final echo signal SEF as illustrated by portion 606 of FIG. 6. The final echo signal SEF thereby represents the total echo for one point (pixel) of the touch surface. The described method will thus have to be performed for each point of the touch surface to be imaged. As mentioned earlier, in many cases it is sufficient to form an image of a selected target area 107, which may be the sub-area of the total touch surface where a finger is placed.

According to one embodiment of the invention, the ultrasonic transducers 106 are configured to introduce a controllable emission delay between consecutive emitted ultrasonic beams, wherein the controllable emission delay is shorter than a period of a sampling frequency of the mixed-signal circuit 203, thereby making it possible to increase the sampling frequency of the mixed-signal integrated circuit 203. FIG. 7 illustrates a first emitted ultrasonic signal 700 and a second emitted ultrasonic signal 702 being emitted with a slight delay $t_d$ between the two signals. Both signals are sampled with the same sampling frequency $f_s$. By combining the responses, the resulting signal 704 is effectively sampled with a higher sampling frequency. In the illustrated example the time delay is equal to half a period of the sampling frequency, i.e. $t_d=(2*f_s)^{-1}$, making the resulting effecting sampling frequency twice the actual sampling frequency.

Even though the invention has been described with reference to specific exemplifying embodiments thereof, many different alterations, modifications and the like will become apparent for those skilled in the art. Also, it should be noted that parts of the system and method may be omitted, interchanged or arranged in various ways, the system and method yet being able to perform the functionality of the present invention.

Additionally, variations to the disclosed embodiments can be understood and effected by the skilled person in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage.

The invention claimed is:

1. An ultrasonic biometric imaging system comprising:
   a cover structure having a touch surface;
   a plurality of ultrasonic transducers arranged at a periphery of the touch surface, the plurality of ultrasonic transducers being configured to emit an ultrasonic beam in the cover structure and to receive reflected ultrasonic echo signals, the reflected ultrasonic echo signals resulting from reflections by an object in contact with the touch surface;

a plurality of mixed-signal integrated circuits, each mixed-signal integrated-circuit being connected to a subset of ultrasonic transducers, wherein each mixed-signal integrated-circuit is configured to:
- analog-to-digital, AD-convert a received analog echo-signal to form a digital echo signal for each active ultrasonic transducer in the subset of ultrasonic transducers;
- perform local beamforming by introducing a first controllable delay to each digital echo signal to form a plurality of delayed echo signals; and
- sum the plurality of delayed echo signals to form an intermediate signal;

wherein the biometric imaging system further comprises:
a host processor connected to each of the plurality of mixed-signal integrated-circuits and configured to:
- receive a plurality of intermediate signals from the plurality of mixed-signal integrated-circuits;
- perform global beamforming by introducing a second controllable delay to each intermediate signal; and
- sum the plurality of delayed intermediate signals to form a final echo signal.

2. The ultrasonic biometric imaging system according to claim 1, wherein the first controllable delay is an individually controllable delay applied to each digital echo signal to form the plurality of delayed echo signals.

3. The ultrasonic biometric imaging system according to claim 1, wherein the second controllable delay is an individually controllable delay applied to each intermediate signal to form the plurality of delayed intermediate signals.

4. The ultrasonic biometric imaging system according to claim 1, wherein the first and second controllable delays introduced during local and global beamforming, respectively, are configured such that the resulting final echo signal represents one pixel of the ultrasonic biometric imaging system.

5. The ultrasonic biometric imaging system according to claim 1, wherein the first controllable delay is shorter than the second controllable delay.

6. The ultrasonic biometric imaging system according to claim 1, wherein the mixed-signal integrated circuit is further configured to interpolate the digital echo signal.

7. The ultrasonic biometric imaging system according to claim 1, wherein the plurality of mixed-signal integrated-circuits are configured to operate in parallel.

8. The ultrasonic biometric imaging system according to claim 1, wherein the ultrasonic transducers are configured to introduce a controllable emission delay between consecutive emitted ultrasonic beams, wherein the controllable emission delay is shorter than a period of a sampling frequency of the mixed-signal circuit.

9. An electronic user device comprising an ultrasonic biometric imaging system according to claim 1.

10. The electronic user device according to claim 9, wherein the cover structure of the ultrasonic biometric imaging system is a display glass of the electronic user device.

11. A method for image acquisition in an ultrasonic biometric imaging device comprising a cover structure having a touch surface and a plurality of ultrasonic transducers arranged at a periphery of the touch surface, the method comprising:
- Emitting, by the plurality of ultrasonic transducers, an ultrasonic beam in the cover structure;
- receiving, by the plurality of ultrasonic transducers, reflected ultrasonic echo signals, the reflected ultrasonic echo signals resulting from reflections by an object in contact with the touch surface;
- analog-to-digital, AD-converting, in a mixed-signal integrated circuit connected to a subset of ultrasonic transducers, a received analog echo-signal and forming a digital echo signal for each active ultrasonic transducer in the subset of ultrasonic transducers;
- performing local beamforming by introducing a first controllable delay to each digital echo signal, thereby forming a plurality of delayed echo signals; and
- summing the plurality of delayed echo signals forming an intermediate signal;
- receiving, by a host processor connected to each of the plurality of mixed-signal integrated-circuits, a plurality of intermediate signals from the plurality of mixed-signal integrated-circuits;
- performing, by the host processor, global beamforming by introducing a second controllable delay to each intermediate signal; and
- summing, by the host processor, the plurality of delayed intermediate signals, thereby forming a final echo signal.

12. The method according to claim 11, further comprising individually controlling the first controllable delay applied to each digital echo signal to form the plurality of delayed echo signals.

13. The method according to claim 11, further comprising individually controlling the second controllable delay applied to each intermediate signal to form the plurality of delayed intermediate signals.

14. The method according to claim 11, further comprising controlling the first and second controllable delays such that the resulting final echo signal represents one pixel of the ultrasonic biometric imaging system.

15. The method according to claim 11, further comprising, by the mixed-signal integrated circuit, interpolating the digital echo signal.

16. The method according to claim 11, further comprising introducing a controllable emission delay between consecutive emitted ultrasonic beams, wherein the controllable emission delay is shorter than a period of a sampling frequency of the mixed-signal circuit.

* * * * *